US011549901B2

(12) United States Patent
Barbul et al.

(10) Patent No.: US 11,549,901 B2
(45) Date of Patent: Jan. 10, 2023

(54) SENSOR COMPONENT AND MOBILE COMMUNICATION DEVICE INCLUDING THE SAME

(71) Applicant: TDK Corporation, Tokyo (JP)

(72) Inventors: Andreas Barbul, Munich (DE); Matthias Koenig, Munich (DE)

(73) Assignee: TDK CORPORATION, Tokyo (JP)

( * ) Notice: Subject to any disclaimer, the term of this patent is extended or adjusted under 35 U.S.C. 154(b) by 332 days.

(21) Appl. No.: 16/956,716

(22) PCT Filed: Dec. 4, 2018

(86) PCT No.: PCT/EP2018/083515
§ 371 (c)(1),
(2) Date: Jun. 22, 2020

(87) PCT Pub. No.: WO2019/120990
PCT Pub. Date: Jun. 27, 2019

(65) Prior Publication Data
US 2020/0400597 A1    Dec. 24, 2020

(30) Foreign Application Priority Data
Dec. 22, 2017    (DE) .......................... 102017131204.8

(51) Int. Cl.
*G01N 27/12*    (2006.01)
*G01N 33/00*    (2006.01)
(Continued)

(52) U.S. Cl.
CPC ......... *G01N 27/123* (2013.01); *G01N 27/028* (2013.01); *G01N 27/045* (2013.01);
(Continued)

(58) Field of Classification Search
CPC .. G01N 27/123; G01N 27/028; G01N 27/045; G01N 27/128; G01N 33/0036; G01N 27/122; G01P 5/12
See application file for complete search history.

(56) References Cited

U.S. PATENT DOCUMENTS 4,472,239 A    9/1984  Johnson et al.
5,581,028 A    12/1996 Barth et al.
(Continued)

FOREIGN PATENT DOCUMENTS

DE    4006085 A1    8/1991
DE    19916797 A1   11/2000
(Continued)

OTHER PUBLICATIONS

Lennart Löfdahl, et al., "Characteristics of a Hot-Wire Microsensor for Time-Dependent Wall Shear Stress Measurements," Preprint of Experiments in Fluids 35, Feb. 23, 2003, pp. 1-13.

*Primary Examiner* — Benjamin R Schmitt
(74) *Attorney, Agent, or Firm* — Slater Matsil, LLP (57) ABSTRACT

A sensor component and a mobile communication device including a sensor component are disclosed. In an embodiment a sensor component includes a subcomponent configured to sense a gas level including a resistive heater and a gas sensitive element disposed on the resistive heater; a package enclosing a cavity and accommodating the subcomponent, the package including a first opening in a position facing the gas sensitive element of the subcomponent and a second opening configured to allow a flow of gas to enter the package through the first opening and exit the package through the second opening; and an evaluation circuit configured to generate an output signal indicative of a speed of the flow of gas in response to electrical power to be supplied to the resistive heater.

14 Claims, 4 Drawing Sheets

(51) Int. Cl.
    *G01P 5/12*     (2006.01)
    *G01N 27/04*     (2006.01)
    *G01N 27/02*     (2006.01)

(52) U.S. Cl.
    CPC ....... *G01N 27/128* (2013.01); *G01N 33/0036* (2013.01); *G01P 5/12* (2013.01)

(56) References Cited

U.S. PATENT DOCUMENTS

| | | | |
|---|---|---|---|
| 6,736,001 | B1 | 5/2004 | Mueller et al. |
| 9,709,425 | B2 | 7/2017 | Matsui et al. |
| 10,228,338 | B2 | 3/2019 | Petersen et al. |
| 2004/0237645 | A1 | 12/2004 | Naguib et al. |
| 2005/0188760 | A1 | 9/2005 | Fujiwara et al. |
| 2014/0105790 | A1* | 4/2014 | Gaudon ............. G01N 27/16 422/90 |
| 2015/0362451 | A1* | 12/2015 | Hunziker .......... G01N 33/0009 73/31.06 |
| 2017/0261455 | A1 | 9/2017 | Paik et al. |

FOREIGN PATENT DOCUMENTS

| | | |
|---|---|---|
| DE | 69528218 T2 | 4/2003 |
| DE | 102014016636 A1 | 5/2015 |
| DE | 102016201950 A1 | 8/2017 |
| DE | 102016203239 A1 | 8/2017 |
| EP | 2533037 A1 | 12/2012 |
| EP | 2765410 A1 | 8/2014 |
| EP | 3139159 A1 | 3/2017 |
| WO | 2009053757 A2 | 4/2009 |
| WO | 2017188700 A1 | 11/2017 |

\* cited by examiner

FIG 5

SENSOR COMPONENT AND MOBILE COMMUNICATION DEVICE INCLUDING THE SAME

This patent application is a national phase filing under section 371 of PCT/EP2018/083515, filed Dec. 4, 2018, which claims the priority of German patent application 102017131204.8, filed Dec. 22, 2017, each of which is incorporated herein by reference in its entirety.

TECHNICAL FIELD

The present disclosure relates to a sensor component to sense a gas. Specifically, the present disclosure relates to a sensor component that includes a resistive heater and a gas sensitive element disposed on the resistive heater that are enclosed in a package. The present disclosure relates further to a mobile communication device that includes such a sensor component.

BACKGROUND

Sensor components that include a gas sensitive element disposed on a resistive heater are used to measure a gas concentration of a reactive gas. The reactive gas may be oxidized or reduced at the surface of the gas sensitive element at an elevated temperature.

There is also a need for wind speed sensors that may be used in various fields of application to detect the speed of a flow of gas in order to display the flow speed on a screen or control a process in response to the measured flow speed. Current devices for the measurement of the flow speed of a gas may employ the principle of a thermo-electronic anemometer, however, such devices have a considerable size so that they are hardly suitable for future applications in mobile electronic devices such as smartphones.

Accordingly, there is a need to have a sensor component to measure the speed of the flow of a gas. Especially, there is a desire to have a sensor component that allows wind speed measurement.

SUMMARY

Embodiments provide a sensor component for the measurement of a flow of gas that has a small size.

Further embodiments provide a sensor component that is sufficiently small to be included in a mobile device such as a mobile communication device or a smartphone.

Yet further embodiments provide a mobile communication device with a sensor component to enable wind speed measurement.

A sensor component according to this disclosure may comprise a subcomponent configured to sense a gas level comprising: a resistive heater and a gas sensitive element disposed on the resistive heater; a package enclosing a cavity and accommodating the subcomponent, the package comprising a first opening in a position facing the gas sensitive element of the subcomponent and a second opening to allow a flow of gas to enter the package through the first opening and exit the package through the second opening; and an evaluation circuit to generate an output signal indicative of the speed of the flow of gas in response to electrical power to be supplied to the resistive heater.

A sensor component that includes a resistive heater and a gas sensitive element that is disposed on the resistive heater is suitably modified so that it can be used for the measurement of the flow speed of a gas while maintaining small size. Whereas such sensor components have previously been used for gas detection measurements only, the present disclosure enables the measurement of the flow speed of a gas or of ambient air wind speed. The package that includes the sensing subcomponent is equipped with at least two openings to allow the entry and the exit of the flow of gas of which the speed is to be measured. The additional evaluation circuit generates the output signal that is indicative of the flow speed in response to the electrical power supplied to the resistive heater. It can be included in an application-specific integrated circuit that may be included within the cavity of the package so that the small size of the sensor is maintained.

The package may comprise a first package portion that encloses a cavity and a second package portion that forms a lid engaged with the first package portion. One opening is disposed in the lid and another opening is disposed in the first package portion that encloses the cavity. The lid may be made of metal or a plastic material, and the first package portion may be made of a plastic material so that the package is easy to manufacture. Other materials are also possible depending on the field of application.

The first package portion may be equipped with one or more electrical contact regions in the bottom sidewall. The sensor subcomponent can be mounted on the bottom sidewall so that the package maintains small dimensions. The electrical contact regions of the package and the corresponding electrical connection terminals at the sensor subcomponent receive electrical power to heat the resistive heater or supply a gas sensing signal.

The connection between the electrical connection terminals of the sensor subcomponent and the electrical contact regions may be achieved by bump contacts such as solder balls, which provide a good and secure electrical and mechanical connection with a small size. Alternatively, instead of bumps or solder balls, bond wires can be used to connect the electrical connection terminals of the sensor subcomponent to the electrical contact regions in the package.

The openings in the package and the gas sensitive element are aligned along one straight direction, for example, perpendicular to the bottom sidewall of the package to allow a gas flow through the sensor and enable wind speed measurement.

Alternatively, one opening may be provided in the lid of the package, and another opening may be provided in a sidewall of the package that is coupled and adjacent to the lid. This allows a flow of gas entering the package through the lid opening and exiting the package through the side opening. Such a package may have a small thickness that can be included in electronic equipment that has a narrow package.

The sensor subcomponent may comprise a substrate and a wire strip that includes the resistive heater. The wire strip is connected to contact terminals through which electrical current can be supplied to the wire strip to heat the resistive heater. Other contact terminals are provided that are connected to the gas sensitive element to generate a sense output signal that is indicative of a detected gas level. The gas may be a reactive gas such as oxygen ($O_2$), nitrooxygen ($NO_x$), carbonmonoxide (CO) that is reduced or oxidized, which chemical reaction inserts or retrieves electrons from the gas sensitive element, which can be sensed.

The sensor subcomponent may have a membrane layer disposed between the substrate and the wire strip. An insulation layer may be disposed between the resistive heater and the gas sensitive element. The gas sensitive element may be a metal oxide that is configured to oxidize or reduce the to be sensed gas at elevated temperature when heated by the resistive heater.

The substrate may have a ring shape configuration wherein the membrane layer has at least one or more openings or etch-throughs, so that the gas can flow through the sensor and allow speed measurements of the gas flow. The openings allow a gas flow perpendicular or with a perpendicular component relative to the plane of the resistive heater and the gas sensitive element. The sensor has an increased sensitivity for changes and variations in the gas flow. The membrane layer is disposed transversal or flat to the direction of the gas flow so that it is cooled efficiently allowing an exact measurement and a dynamic measurement of the gas flow velocity that allows an accelerated response to changes in the gas flow velocity.

The contact terminals of the subcomponent for the supply of electrical power may be disposed on the substrate along a first direction and the contact terminals for the gas measurement may be disposed on the substrate along a second direction crossing the first direction. For example, the first and the second directions may have a perpendicular relation. The membrane layer has a strip shape with respective openings that allow a flow of gas through the sensor. The strips are oriented along the first and second directions.

A control circuit loop is employed to control the electrical power for the resistive heater to maintain the temperature of the resistive heater. The control loop regulates the electrical power so that the temperature of the resistive heater is maintained constant or at least substantially constant so that a reliable gas level management is possible. A sensing circuit is connected to those contact terminals that are connected to the gas sensitive element. The sensing circuit provides a signal which is indicative of the amount of reactive gas such as $O_2$, CO, $NO_x$ that is sensed by the gas sensor component at the elevated temperature of the resistive heater. A suitable temperature is in the range of 300° C.

The control loop uses a signal that represents the resistance of the resistive heater which resistance depends on the temperature of the resistive heater. For example, the resistance of the resistive heater may decrease with decreasing temperature and the control circuit loop may use a voltage dependent on the resistance of the resistive heater. This signal may be used as a feedback to a controllable current source that supplies current to the resistive heater. The control loop may increase the current in response to said voltage to maintain the temperature and, therefore, the resistance of the resistive heater will be regulated substantially constant.

By way of theoretical explanation, the flow of gas passing the resistive heater removes heat from the heater and cools the heater. The control loop is designed such that it supplies additional current to maintain the temperature of the resistive heater and maintain its resistance, using the fact that the resistance of the resistive heater is temperature-dependent. Accordingly, the amount of gas flow or amount of wind passing the sensor component will cool the elements in the sensor component. The control loop leads to an increased electric power so as to maintain the temperature, for example, in the range of 300° C. The amount of electrical power to be supplied is, therefore, indicative of the wind speed of the gas flowing through the sensor component.

In order to supply a signal indicative of the wind speed or the speed of the flow of gas through the sensor, the evaluation circuit generates a corresponding signal that is determined in response to the electrical power supplied to the resistive heater. The evaluation circuit may provide a signal to a display device to depict the wind speed information measured by the sensor device. For example, the evaluation circuit may calculate a linear or non-linear or even proportional relation between the amount of electrical power supplied to the resistive heater and the wind speed. Such a calculation may be performed by a processor or by a predetermined look-up table in the evaluation circuit. The evaluation circuit, therefore, is rather simple and may be realized as an integrated circuit so that it has small dimensions and may be included in the package of the sensor component.

A skilled person will realize that the sensing of the level of a specific gas and the sensing of the wind speed are substantially independent from each other, because the gas level sensing is performed by the gas sensitive element and the wind speed sensing signal is obtained from the control loop for maintaining the temperature of the resistive heater substantially constant. On the other hand, the circuitry for the gas level measurement and the circuitry for the wind speed measurement may be realized in integrated form, so that any additional effort to combine both measurements on one or more integrated circuits is relatively low. Because this circuitry may be integrated, the occupied volume is low so that the integrated circuit(s) can be enclosed in the package of the sensor component. Accordingly, the present embodiment of this disclosure achieves a combined sensor component for the measurement of the level of a reactive gas and the speed of the flow of this gas or its wind speed wherein the dimensions of the package need not be increased. The dimensions may be sufficiently small that a sensor component according to this disclosure fits into the housing of a mobile electronic device. Specifically, a sensor component according to this disclosure may be incorporated in the housing of a mobile communication device such as a cell phone or a smartphone.

One or more of the above-mentioned objects are furthermore achieved with a mobile communication device that comprises: a housing; an electronic circuit disposed in the housing and configured to communicate with a mobile communication network; the above-mentioned sensor component, wherein the sensor component is disposed in the housing and the housing comprises openings that face a respective one of the first and second openings disposed in the package of the sensor component.

The package of the sensor component has two openings which allow entry and exit of a gas flow. When the housing of the mobile communication device has respective openings that are opposite the openings in the package of the sensor component, the gas can flow through the housing of the mobile communication device and can pass the sensor component. This allows wind speed measurement of the gas flow and, in parallel, also the measurement of the gas level. The measurement signals can be supplied to the processor of the mobile communication device and can use its very convenient display capabilities, for example, a mobile phone display screen. This enables an easy and convenient measurement of a gas level and/or the wind speed.

In more detail, the sensor component may be mounted on a printed circuit board and may be connected to the wires of the printed circuit board to receive electrical power from the battery of the mobile communication device and return measurement signals to the processor and the display screen. The printed circuit board may have an opening that faces a corresponding of the openings in the package of the sensor component so that all openings in the package, the housing and the printed circuit board of the mobile communication device are aligned along a direction to allow a gas to flow through the mobile communication device and through the sensor. Sealing elements like O-rings may be disposed between the walls of the housing of the mobile communication device and the upper lid of the package and the printed circuit board so that the openings in the housing of the mobile communication device are sealed against entry of the gas or entry of humidity, etc. into the interior of the housing.

While the present disclosure describes the application of the sensor component in connection with a mobile communication device such a cell phone or a smartphone, the incorporation of the sensor component into other electronic equipment or electronic systems or processing systems is also conceivable.

For example, the sensor component may be also used in wearables or in components adapted for use in the Internet of Things. The sensor may be used in the automotive area as a sensor to determine open windows in a car to cause closing of the windows and avoid unpleasant air flow. The sensor may also be used in an interior area of, for example, a car to control the power of an air conditioning system or a fan or a ventilator.

The package of the sensor component may be further equipped with additional sensors such as humidity sensors, pressure sensors, or microphones that are usually small enough to fit into the package and to enable combined measurements.

The sensor component according to the present disclosure may be used in an aircraft to measure the aircraft velocity by wind speed measurement.

The sensor component may be used in connection with control circuits according to Industry 4.0-applications. For example, the sensor component may measure the quality of air in furnaces and all processes where air flow or air quality need to be measured, for example, when monitoring the air in a food manufacturing facility.

On motor vessels, the quality of the air may be monitored on deck, such as diesel exhaust fumes. Also the wind speed may be measured on deck.

Furthermore, the sensor component according to the present disclosure may be used in drones, such as unmanned aerial vehicles to control their flight behavior.

BRIEF DESCRIPTION OF THE DRAWINGS

It is to be understood that both the foregoing general description and the following detailed description are merely exemplary, and are intended to provide an overview or framework to understand the nature and character of the claims.

The accompanying drawings are included to provide a further understanding and are incorporated in and constitute a part of this description. The drawings illustrate one or more embodiments, and together with the description serve to explain principles and operation of the various embodiments.

In the drawings.

DETAILED DESCRIPTION OF ILLUSTRATIVE EMBODIMENTS

The present disclosure will now be described more fully hereinafter with reference to the accompanying drawings showing embodiments of the disclosure. The disclosure may, however, be embodied in many different forms and should not be construed as limited to the embodiments set forth herein. Rather, these embodiments are provided so that the disclosure will fully convey the scope of the disclosure to those skilled in the art. The drawings are not necessarily drawn to scale but are configured to clearly illustrate the disclosure.

Figure 1:
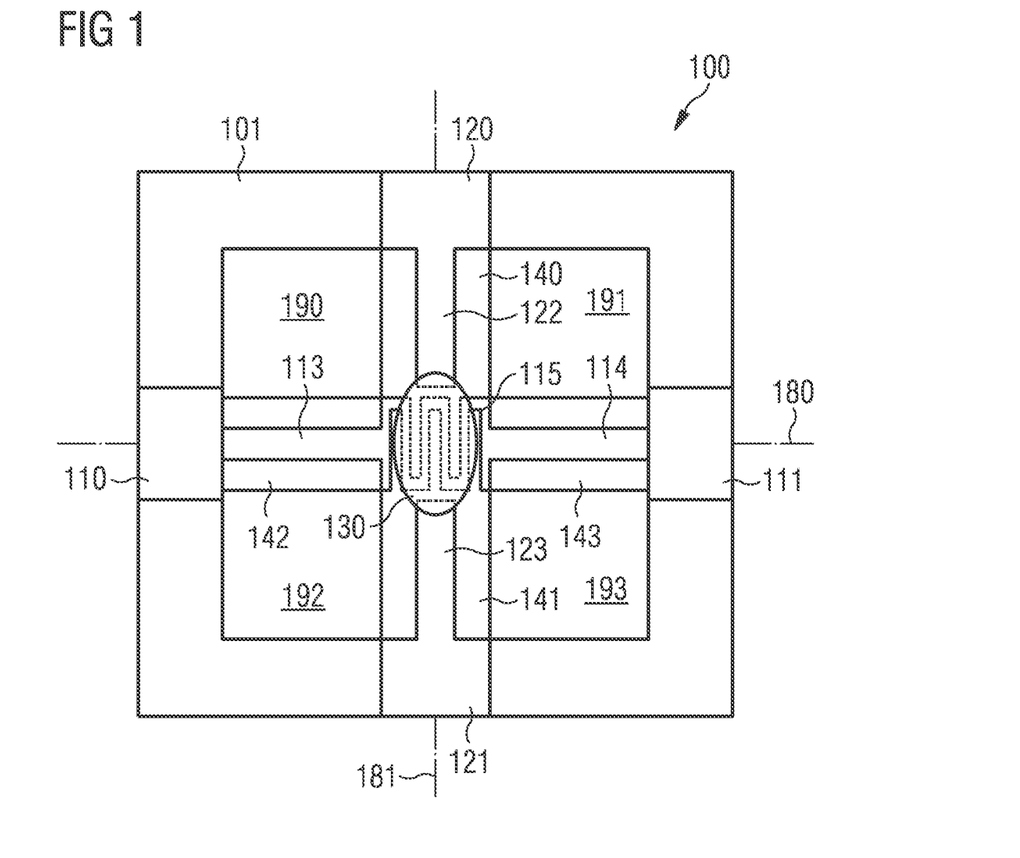
FIG. 1 shows the top view onto a sensor subcomponent.

FIG. 1 shows a top view onto the subcomponent for sensing a gas level, the operation of which is explained in connection with the electrical circuit diagram shown in FIG. 5. The subcomponent 100 of FIG. 1 comprises a substrate ring 101 which has a rectangular shape. Another ring-shape form may also be possible. On the substrate 101 are disposed first and second contacts 110, 111 which are connected to a respective heater strip 113, 114. The heater strips 113, 114 are connected to a resistive heater element 115 which has the form of a meander. Another form is also possible to achieve a heating section having a suitable amount of space or area. If electrical power is supplied to terminals 110, in, the resistive meander heating area 115 is heated to an elevated temperature. The temperature may be at or around 300° C.

Figure 5:
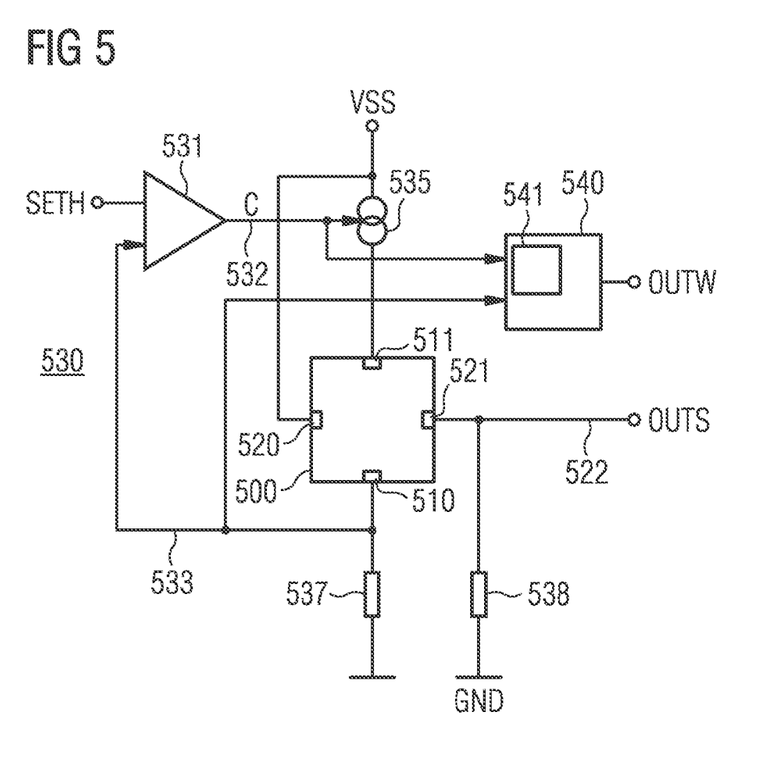
FIG. 5 shows an electronic circuit diagram including the sensor component.

As shown in FIG. 5, the subcomponent 100 is included in package 500 which has terminals 510, 511 to supply subcomponent 500 with electrical power. Terminal 510 is connected to ground potential GND through resistor 537. Terminal 511 is connected to positive supply voltage VSS and is supplied with electrical current from controllable current source 535. Operational amplifier (op-amp) 531 generates a control signal C on its output 532 to control the current of controllable current source 535. Resistor 537 converts the current into a voltage of a suitable range. The op-amp 531 compares the voltage at terminal 510 supplied by line 533 with a reference voltage SETH. Reference signal SETH sets the temperature to be achieved at the meander heating section 115 in subcomponent 100, e.g., 300° C. Thus, a control loop 530 controls the amount of current to be supplied by current source 535 so as to achieve and maintain the resistive heater 115 at the defined temperature.

The heater 115 has an ohmic resistance that varies with temperature. For example, when the temperature becomes lower, the resistance becomes lower, and when the temperature becomes higher, the resistance becomes higher. The signal on line 533 is, therefore, an indicator for the resistance and, consequently, for the temperature of the resistive meander heater 115. The control loop 530 has the function to maintain the temperature of the resistive heater 115 constant or at least substantially constant, such that little temperature variations do not jeopardize the sensing function of subcomponent 100.

Returning to FIG. 1, there is a membrane or support layer 140, 141, 142, 143, on which the heater strips 113, 114 and the resistive meander heater 115 are disposed. Above the meander area 115 is disposed a gas sensitive element 130 so that, during operation, the gas sensitive element 130 can be maintained at the elevated temperature. An insulation layer may be disposed between meander heater 115 and gas sensitive element 130 for electrical isolation. Contacts 120, 121 are connected through respective lines 122, 123 to the gas sensitive element 130. The terminals no, 111 to supply electrical power are aligned along a first direction 180, and the terminals 120, 121 connected to the gas sensitive element 130 are aligned along a second direction 181. First and second directions 180, 181 cross each other and have preferably perpendicular orientation with each other so that the orientation of the mentioned terminals and the form of the heater strips and also the form of the strips of the membrane layer 140, . . . , 143 are cross-shaped or cross-like.

The material of the gas sensitive element 130 may be a metal oxide material such as gallium oxide or tin oxide, or other metallic oxides. At an elevated temperature, gases such as oxygen, carbon-monoxide or nitrogen-oxide are oxidized or reduced on the heated surface of the gas sensitive element and inject or retrieve electrons therefrom, which effect can be sensed at the terminals 120, 121. A suitable temperature for operation is at or about 300° C. This temperature is achieved by controlling the current supplied to terminals 110, 111 through control loop 130 as explained in connection with FIG. 5. Depending on the material of the sensor component, another temperature may be useful to perform a proper sensing function.

Again turning back to FIG. 5, terminal 521 is connected to gas sensor component 130 through terminal 121 on the one hand and is connected through resistor 538 to ground GND. Resistor 538 converts the current from terminal 521 into a voltage. Accordingly, sense output signal OUTS at terminal 522 is indicative of the amount of gas sensed at gas sensor 130. Terminal 520 is connected to terminal 120 of the sensor subcomponent and is supplied with supply voltage VSS. In operation, heating the gas sensitive element 130 by resistive meander heater 115 through control loop 530 and maintaining it at elevated temperature, e.g., 300° C., allows a sensing of reactive gases through output signal OUTS at terminal 522.

Turning back to FIG. 1, sub-unit 100 is supplied with openings 190, 191, 192, 193 in the membrane layer 140, . . . , 143. Any portions of the membrane layer in the areas 190, . . . , 193 have been removed or completely etched to achieve the openings 190, . . . , 193. The subcomponent 100 is, therefore, configured to allow a flow of gas through the paths enabled by openings 190, . . . , 193. The flow of gas includes a component perpendicular or vertical to the gas sensitive element 130. The measurement of the gas flow velocity can thus be performed very sensitive and the measurement reacts more sensitive and more dynamic in response to changes. The measurement of the gas flow is more exact. The measurement is more responsive. Also the membrane layer 140, . . . , 143 is disposed transversal or perpendicular to the gas flow so that the membrane layer is efficiently cooled by the gas flow which makes the response of the measurement to changes more agile and dynamic.

The gas flow removes heat from the resistive meander heater 115 so that the resistive meander heater 115 gradually cools down to a temperature lower than the target temperature of, for example, 300° C., when subjected to a gas flow. Therefore, the ohmic resistance of the resistive heater, which is temperature dependent, gradually decreases, which is sensed through line 533 so that the control loop 530 supplies more current to the power terminals 110, 111 to maintain the target temperature. It is to be assumed that the stronger the flow of gas through the openings 190, . . . , 193, the larger the cooling of the resistive meander heater 115 and the larger the electrical current and electrical power necessary to be supplied to heater 115 to maintain the elevated target temperature. The electrical power supplied to terminals 110, 111 can thus be used as an indicator for the speed of the gas flowing through the openings 190, . . . , 193 or the wind speed to which the gas sensor is subjected to.

Turning back again to FIG. 5, an evaluation 540 is provided which measures the electrical power supplied to terminals 510, 511 and to terminals 110, 111. Evaluation circuit 540 is connected to output 532 of the op-amp 531 and is furthermore connected to line 533 which senses the voltage at resistive heater 115. Therefore, evaluation circuit 540 can calculate the supplied power from signal C on line 532 and the voltage from line 533.

The power to be supplied to terminals 110, 111 may be proportional to the wind speed through openings 190, . . . , 193 or may have another linear or non-linear relation to the to be supplied power. This relation may be used to provide an output signal OUTW at the output of evaluation circuit 540. The transformation from the supplied electrical power to the corresponding wind speed information is performed by circuit 541 which may be a look-up table or the realization of the corresponding linear or non-linear function between electrical power and wind speed. In an ideal case, circuit 541 performs a proportional function.

The described sensor component and the described circuit of FIGS. 1 and 5 allow a double function of measuring a gas level of a reactive gas and measuring the wind speed of the flow of the gas through the sensor. Both measurements can be made in parallel and are substantially independent from each other. The sensor can, therefore, perform the double function of gas sensing and wind speed measuring only requiring little additional circuitry for the evaluation unit 540 and the corresponding connections. The circuitry of FIG. 5 may be implemented in an integrated application-specific circuit which is small enough to be incorporated in the below described housing of the sensor. Accordingly, the sensor has small dimensions so that it can be incorporated in thin electronic devices having narrow housings such as smartphones as described hereinbelow.

Figure 2:
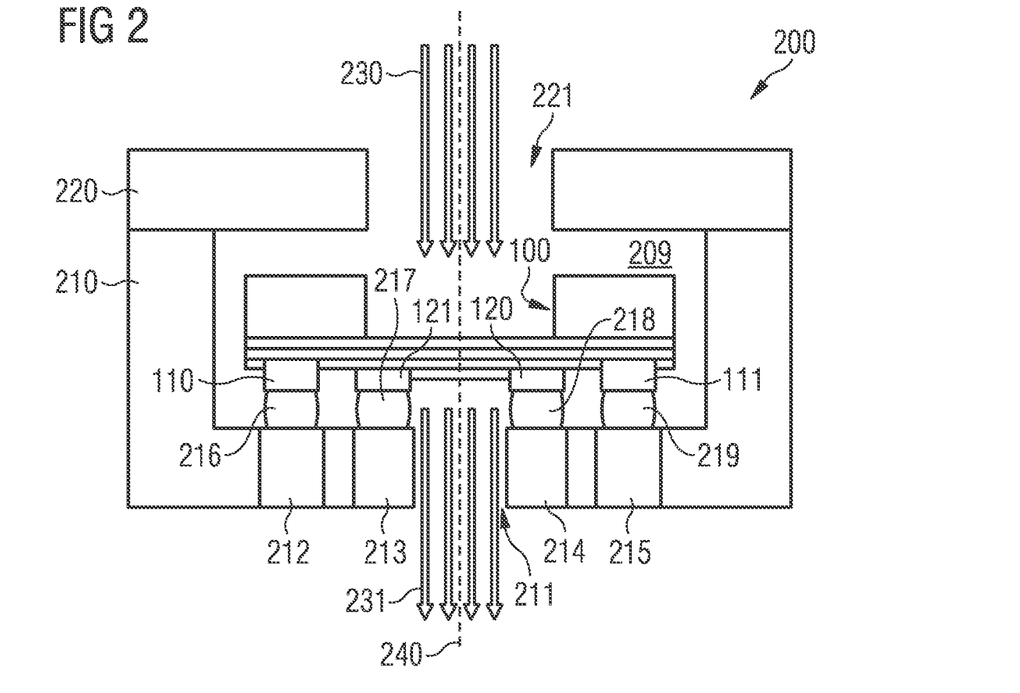
FIG. 2 shows a cross-sectional view of a sensor component, including sensor subcomponent and package.
Figure 3:
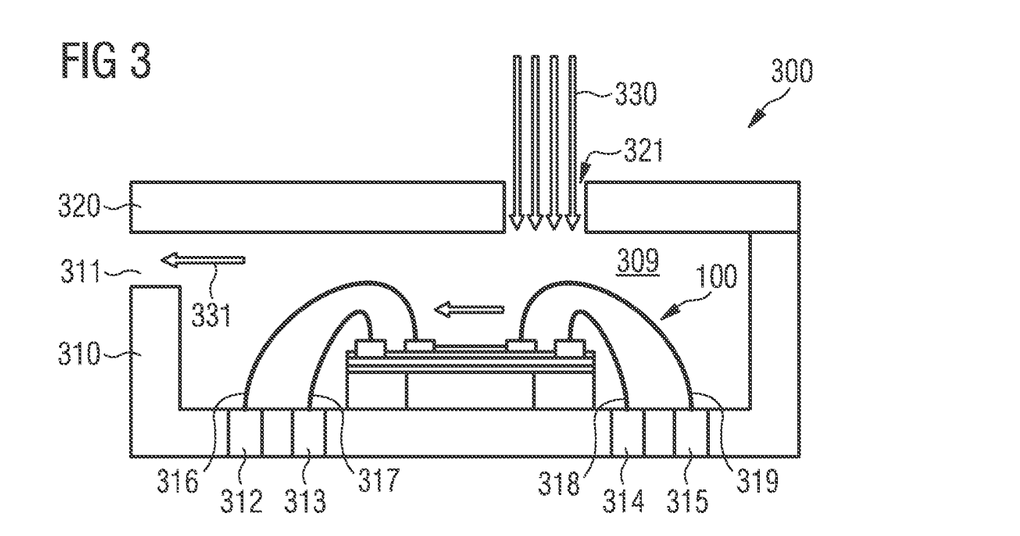
FIG. 3 shows a cross-sectional view of another embodiment of a sensor component.

In FIGS. 2 and 3, cross-sectional views of two embodiments of the sensor component are shown including the sensor subcomponent surrounded by a package.

FIG. 2 shows a subcomponent 200 mounted in a package. The package comprises a first package portion 210 which has side and bottom walls that enclose a cavity 209. The first package portion is covered by a second portion 220 serving as a lid, which is positioned on top of the first package portion 210. The first package portion may be made of a first material such as a plastic material, for example, an extruded polymer material, and the lid package portion 220 may be made of a metal. Other materials for the package portion and combinations of materials are also possible.

The bottom sidewall of the first package portion 210 includes electrical contacts 212, 213, 214, 215. These electrical contacts cooperate with the corresponding contact terminals 110, 121, 120, 111 of the subcomponent 100. The contact terminals of subcomponent 100 are fixed on the electrical contacts in the bottom sidewall of the housing by corresponding solder balls 216, 217, 218, 219. Other ways of connection apparent to a skilled person are also possible. With these connections, the power supply, the voltage to be measured at the resistive meander portion 115 and the signal sensing a gas component at the oxometallic sensor component 130 are accessible at the outside of the package.

The bottom sidewall of the package includes a through-hole 211 and the top lid includes another through-hole 221.

Through-holes 211 and 221 are aligned along a direction 240. The oxometallic sensor component 130 and the resistive meander heater 115 are also aligned with the direction 240. Therefore, a gas flow 230 can be established entering the lid portion 220 of the package through through-hole 221 and exiting the package through the bottom through-hole 211 as exiting gas flow 231. As described in connection with FIGS. 1 and 5, the gas flow 230, 231 will cool the heater 215 so that the control loop increases the supplied power to maintain the temperature at around 300° C. The increased amount of supply power can be used to generate a signal which is indicative of the wind speed of the gas flow 230, 231. As depicted in FIG. 1, it is useful to make the through-hole 221 larger in diameter than the through-hole 211. However, both holes can have the same diameter, or hole 211 can have a larger diameter than hole 221, depending on the application for which the sensor component is designed.

FIG. 3 shows a different embodiment which has a through-hole 321 in the lid portion 320 of the package wherein the exit through-hole 311 of the package is in the lower portion 310, which encloses cavity 309, however, disposed at a sidewall of the bottom portion adjacent to or in contact with the top lid 320. A gas flow 330 may enter the package through the top lid through-hole 321 and will pass the sensor subcomponent 100 at its surface and will exit the package by through-hole 311 as exiting gas flow 331. The connection of the terminals of the subcomponent 100 to the electrical terminals 312, 313, 314, 315 in the bottom sidewall of the package is performed with bond wires 316, 317, 318, 319. Alternatively, solder balls could also be used in this embodiment.

It is useful to provide the subcomponent 100 of the arrangement depicted in FIG. 2 with windows 190, 191, 192, 193 in the membrane layer as shown in FIG. 1 so that the gas flow can pass through the windows in the subcomponent 100. The subcomponent 100 of the arrangement depicted in FIG. 3 may be used without such windows because the gas flow passes at the top surface of the subcomponent. In this case the subcomponent has now windows and the substrate ring is completely covered with a membrane layer (not shown).

Figure 4:
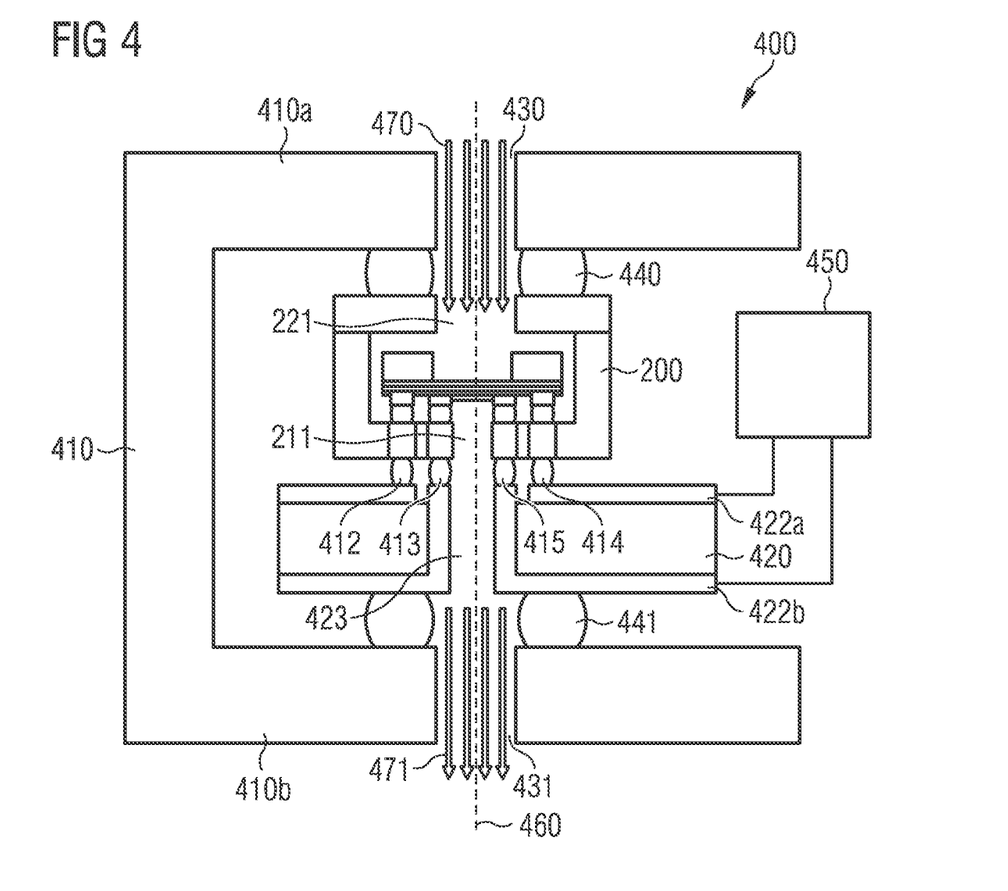
FIG. 4 shows a sensor component mounted on a printed circuit board and included in a housing of a mobile communication device.

FIG. 4 shows the application of a sensor component according to the principles of this disclosure in the field of electronic devices such as mobile communication device or cell phones or smartphones. The packaged sensor component 200 is mounted on a printed circuit board 420. The contact areas in the bottom sidewall of package 200 are connected to the metal wires 422a, 422b on the printed circuit board by corresponding solder balls 412, 413, 414, 415. The wires 422a, 422b are connected to the internal electronic circuitry 450 of the smartphone 400. The circuitry 450 may include the processor of the smartphone which may be used to display the sense signals received from the sensor component 200 on the display screen of the smartphone so that the measurement of the gas level and the windspeed can benefit from the enhanced graphical display capabilities of the smartphone.

The arrangement of component 200 and circuit board 420 is sandwiched between top and bottom walls 410a, 410b of the smartphone. A through-hole 430 is included in top wall 410a and a through-hole 431 is included in bottom wall 410b of the housing. Another through-hole 423 is included in the printed circuit board 420. All through-holes, e.g., the through-holes 430, 341 through top and bottom wall of the housing, the through-holes 221, 211 through the top lid and bottom sidewall of the package of the sensor component 200 and through-hole 423 through the printed circuit board are aligned along a direction 460. An air flow 470 may enter the housing through through-hole 430 and exit the housing through through-hole 431 as exiting air flow 471 thereby passing the sensor subcomponent in the package 200. Accordingly, the smartphone 400 has the capability to sense the level of a specific gas concentration in the air and at the same time has the capability to measure and display the wind speed of the entering and exiting air flow 470, 471 by the arrangements and measurement processes described above.

The gap between the top lid of the package of the sensor component and the top wall 410a of the housing is sealed with sealing ring 440, which may be an O-ring. In the same way, the gap between the bottom side of the printed circuit board 420 and the bottom wall 410b of the housing is sealed by sealing ring 441 so that the air flow propagates along direction 460 and does not enter the other interior portions of the smartphone. Furthermore, the sealing rings 440, 441 clamp the sensor component and the printed circuit board between top and bottom walls of the smartphone housing.

The space in a mobile application such as a smartphone is a critical point. The packaged sensor component according to the present disclosure has small dimensions so that it fits into the thin width of the smartphone housing. The oxometallic gas sensor is adapted as a dual use sensor which can measure a gas concentration and can measure the wind speed of an air flow. Fields of application for the sensor component other than mobile communication devices have been explained above.

In summary, the sensor component according to the present disclosure comprises a subcomponent 100 that is configured to sense a gas level that comprises a resistive heater 115 and a gas sensitive element 130. A package accommodates the subcomponent wherein the package comprises openings 211, 221 that allow a gas flow to enter and exit the package. An evaluation circuit may generate an output signal which is indicative of the speed of the flow of gas in response to the electrical power to be supplied to the resistive heater.

It will be apparent to those skilled in the art that various modifications and variations can be made without departing from the spirit or scope of the disclosure. Since modification combinations, sub-combinations, and variations of the disclosed embodiments incorporating the spirit and substance of the disclosure may occur to persons skilled in the art, the disclosure should be construed to include everything within the scope of the appended claims.

The invention claimed is:

1. A sensor component comprising:
 a subcomponent configured to sense a gas level comprising:
  a ring-shaped substrate enclosing an inner area;
  a resistive heater;
  a wire strip connected to the resistive heater;
  a gas sensitive element disposed on the resistive heater; and
  a membrane layer disposed between the substrate and the wire strip having at least one opening configured to enable a gas flow through the at least one opening and through the inner area;
 a package enclosing a cavity and accommodating the subcomponent, the package comprising:
  a first opening in a position facing the gas sensitive element of the subcomponent; and
  a second opening configured to allow a flow of gas to enter the package through the first opening and exit the package through the second opening; and an evaluation circuit configured to generate an output signal indicative of a speed of the flow of gas in response to electrical power to be supplied to the resistive heater.

2. The sensor component of claim 1, wherein the package comprises a first package portion enclosing the cavity and a second package portion forming a lid engaged with the first package portion, and wherein the first opening is disposed in the second package portion and the second opening is disposed in the first package portion.

3. The sensor component of claim 2, wherein the first package portion has a bottom sidewall that faces the second package portion, the bottom sidewall comprising one or more electrical contact regions, wherein the subcomponent is mounted on the bottom sidewall and comprises electrical connection terminals configured to receive electrical current to heat the resistive heater and electrical connection terminals configured to output a gas sensing signal, and wherein each one of the electrical connection terminals is connected to a respective one of the one or more electrical contact regions.

4. The sensor component according to claim 3, further comprising at least one solder contact that connects each one of the electrical connection terminals to a respective one of the one or more electrical contact regions.

5. The sensor component according to claim 3, further comprising at least one bond wire that connects each one of the electrical connection terminals to a respective one of the one or more electrical contact regions.

6. The sensor component according to claim 3, wherein the second opening is provided in the bottom sidewall of the first package portion, and wherein the first opening, the second opening and the gas sensitive element are aligned along one direction.

7. The sensor component according to claim 2, wherein the second opening is provided in a sidewall of the first package portion that is adjacent to the second package portion.

8. The sensor component according to claim 1, wherein the subcomponent further comprises:
   a first contact terminal and a second contact terminal connected to the wire strip configured to supply electrical current to the wire strip to heat the resistive heater; and
   a third contact terminal and a fourth contact terminal connected to the gas sensitive element configured to output a sense output signal that is indicative of a reactive gas detected by the gas sensitive element.

9. The sensor component according to claim 8, wherein the gas sensitive element is made of a metal oxide configured to oxidize or reduce a to be sensed gas when heated by the resistive heater.

10. The sensor component according to claim 8, wherein the first and second contact terminals are disposed on the substrate along a first direction and the third and fourth contact terminals are disposed on the substrate along a second direction crossing the first direction, and wherein the membrane layer extends stripwise along the first and second directions and does not exists in an area outside of the strips.

11. The sensor component according to claim 10,
   wherein the resistive heater has a resistance that depends on a temperature of the resistive heater, a control circuit loop being connected to at least one of the first and second contact terminals to obtain a signal indicative of the resistance of the resistive heater,
   wherein a controllable current source is connected to one of the first and second contact terminals to maintain the resistance of the resistive heater so that the resistance is substantially constant in response to the signal indicative of the resistance of the resistive heater, and
   wherein the evaluation circuit generates the output signal indicative of the speed of the flow of gas to enter and to exit the package in response to the electrical power supplied to the first and second contact terminals.

12. The sensor component according to claim 8, further comprising:
   a control circuit loop configured to control the electrical power to be supplied to the resistive heater to maintain a temperature of the resistive heater so that the temperature is substantially constant; and
   a sensing circuit connected to at least one of the third and fourth contact terminals configured to provide a signal indicative of an amount of the reactive gas sensed by the gas sensitive element when heated by the resistive heater.

13. A mobile communication device comprising:
   a housing;
   an electronic circuit disposed in the housing and configured to communicate with a mobile communication network; and
   the sensor component according to claim 1,
   wherein the sensor component is disposed in the housing, and
   wherein the housing comprises openings that face a respective one of the first and second openings disposed in the package of the sensor component.

14. The mobile communication device of claim 13, further comprising:
   a printed circuit board; and
   first and second sealing elements each disposed within the housing,
   wherein the sensor component is disposed on the printed circuit board and is electrically connected to wires disposed on the circuit board,
   wherein the printed circuit board has an opening facing the second opening in a first package portion of the sensor component,
   wherein the housing has a first opening and a second opening,
   wherein the first and second openings of the housing, the first and second openings of the package portions of the sensor component and the opening of the circuit board are aligned along a direction so that the gas flow is able to enter the housing through one of the first and second openings in the housing and exit the housing through the other one of the first and second openings in the housing,
   wherein the first sealing element is disposed between one wall of the housing and the second package portion of the sensor component to enclose the respective openings in the second package portion of the sensor component and the first opening in the housing,
   wherein the second sealing element is disposed between another wall of the housing and the printed circuit board enclosing the opening in the circuit board and the second opening in the other wall of the housing, and
   wherein the first and second sealing elements are configured to prevent gas from entering an internal space of the housing.

* * * * *